US006878943B2

(12) United States Patent
Tao et al.

(10) Patent No.: US 6,878,943 B2
(45) Date of Patent: Apr. 12, 2005

(54) HEXAVALENT CHROMIUM MONITOR

(75) Inventors: Shiquan Tao, Starkville, MS (US); Christopher B. Winstead, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 96 days.

(21) Appl. No.: 10/227,191

(22) Filed: Aug. 22, 2002

(65) Prior Publication Data

US 2004/0036028 A1 Feb. 26, 2004

(51) Int. Cl.$^7$ .................................................. G01J 1/42
(52) U.S. Cl. ...................... 250/373; 250/372; 250/336.1
(58) Field of Search ................................ 250/373, 372, 250/336.1

(56) References Cited

U.S. PATENT DOCUMENTS

| | | | | |
|---|---|---|---|---|
| 5,416,879 A | | 5/1995 | Liu | 385/125 |
| 5,444,807 A | * | 8/1995 | Liu | 385/125 |
| 5,570,447 A | | 10/1996 | Liu | 385/125 |
| 5,646,863 A | * | 7/1997 | Morton | 702/23 |
| 6,011,882 A | | 1/2000 | Dasgupta et al. | 385/12 |
| 6,016,372 A | | 1/2000 | Fein et al. | 385/12 |
| 6,104,485 A | * | 8/2000 | Wang et al. | 356/246 |
| 6,188,813 B1 | | 2/2001 | Dourdeville et al. | 385/12 |
| 6,332,049 B1 | * | 12/2001 | Dasgupta | 385/12 |
| 6,385,380 B1 | * | 5/2002 | Friedrich et al. | 385/125 |
| 6,603,556 B2 | * | 8/2003 | Belz et al. | 356/440 |
| 6,797,179 B2 | * | 9/2004 | Arnaud | 210/709 |
| 2003/0001974 A1 | * | 1/2003 | Viltchinskaia et al. | 204/400 |

OTHER PUBLICATIONS

C. Whalley, et al., Chromium Speciation in Natural, Waters Draining Contaminated Land, Glasgow, U.K., 112 Water, Air, and Soil Pollution, 389–405 (1999).

E.C. Thornton, et al., Hydrogen Sulfide Gas Treatment of CR(VI)–Contaminated Sediment Samples from a Plating–Waste Disposal Site—Implications for In–Situ Remediation, 33 Environmental Science & Technology, 4096–01 (1999).

C.T. Dillon, et al., Permeability, Cytotoxicity, and Genotoxicity of Chromium (V) and Chromium (VI) Complexes in V79 Chinese Hamster Lung Cells, 11 Chemical Res. Toxicology, 119–129 (1998).

G. Quiervyn, et al., Carcinogenic Chromium (VI) Induces Cross–Linking of Vitamin C to DNA In Vitro and in Human Lung A549 Cells, 41 Biochemistry 3156–3167 (2002).

S. Tao, et al., Volatilization of Refractory Elements as 8–Hydrozyquinolinate Complexes for Sample Introduction in Inductively Coupled Plasma Atomic Emission Spectrometry, 32 Analytical Proceedings Including Analytical Communications, 371–373 (1995).

(Continued)

Primary Examiner—David Porta
Assistant Examiner—Christine Sung
(74) Attorney, Agent, or Firm—Needle & Rosenberg, P.C.

(57) ABSTRACT

A monitor is provided for use in measuring the concentration of hexavalent chromium in a liquid, such as water. The monitor includes a sample cell, a light source, and a photodetector. The sample cell is in the form of a liquid-core waveguide, the sample cell defining an interior core and acting as a receiver for the liquid to be analyzed, the interior surface of the sample cell having a refractive index of less than 1.33. The light source is in communication with a first end of the sample cell for emitting radiation having a wavelength of about and between 350 to 390 nm into the interior core of the waveguide. The photodetector is in communication with a second end of the waveguide for measuring the absorption of the radiation emitted by the light source by the liquid in the sample cell. The monitor may also include a processor electronically coupled to the photodetector for receipt of an absorption signal to determine the concentration of hexavalent chromium in the liquid.

54 Claims, 5 Drawing Sheets

OTHER PUBLICATIONS

R.E. Clement, et al., Environmental Analysis, 71 Analytical Chemistry 257R–292R (1999).

M.H. Crawford, et al., Design and Performance of Nitride–Based UV LEDs, 3938 SPIE 13–23 (2000).

D.A. Skoog, et al., Fundamentals of Analytical Chemistry, 506–519 (7th ed., Saunders College Publishing).

TEFLON® AF: A New Generation of High–Performance Fluoropolymer Resins, DuPont De Nemours and Company (2002).

R. Altkorn, et al., Low–Loss Liquid–Core Optical Fiber for Low–Refractive–Index Liquids: Fabrication, Characterization, and Application in Raman Spectroscopy, 36 Applied Optics 8992–8998 (1997).

P.K. Dasgupta, et al., High–Sensitivity Gas Sensors Based on Gas–Permeable Liquid Core Waveguides and Long–Path Absorbance Detection, 70 Analytical Chemistry 4661–4669 (1998).

R. Altkorn, et al., Raman Performance Characteristics of Teflon®–AF 2400 Liquid–Core Optical–Fiber Sample Cells, 53 Applied Spectroscopy 1169–1176 (1999).

B.J. Marquardt, et al., A Raman Waveguide Detector for Liquid Chromatography, 71 Analytical Chemistry 4808–4814 (1999).

J. Li, et al., Measurement of Atmospheric Hydrogen Peroxide and Hydromethyl Hydroperoxide with a Diffusion Scrubber and Light Emitting Diode—Liquid–Core Waveguide–Based Fluorometry, 72 Analytical Chemistry 5335–5347 (2000).

Z. Marczenko ED., Spectrophotometric Determination of Elements, 213–23 (John Wiley & Sons, Inc., New York). (1976).

* cited by examiner

HEXAVALENT CHROMIUM MONITOR

This invention was made with U.S. Government support under Contract No. DE-FC26-98FT-40395 awarded by the Department of Energy. The U.S. Government may have certain rights in this invention.

BACKGROUND OF THE INVENTION

1. Field of the Invention

This invention relates, generally, to the field of detecting and/or monitoring chromium contamination and, more particularly, to a hexavalent chromium ("Cr(VI)") monitor for detecting and/or continuously monitoring the concentration of Cr(VI) in a liquid such as water.

2. Background Art

Chromium and its compounds are primarily used in the manufacture of steel and other alloys, chrome plating, pigment production and leather tanning. In addition, chromate salts have been used for many years as excellent reagents in chemical laboratories. In the past, the hazardous characteristics of chromate compounds were not adequately recognized, so that chromium-containing waste was often inadequately disposed. At present, leaching of chromium compounds from waste sites to ground water has caused water contamination all around the world. Drinking water contamination has been reported in many places in the U.S.

Chromium can exist in nature as a compound in one of two stable valences. Chromium in trivalent chromium ("Cr (III)") compounds is nontoxic and is actually an essential nutrient for the human body. Chromium in Cr(VI) compounds is known to be carcinogenic. Therefore, chromium contamination is actually a problem of Cr(VI) contamination. In water contamination investigations and contamination control, what is important is the concentration of Cr(VI) in the water.

Present laboratory analytical methods for chromium detection include, for example, inductively coupled plasma atomic emission spectrometry ("ICP-AES"), which can detect chromium in water to part-per-billion (ppb) levels. See, S. Tao and T. Kumamaru, *Anal. Proc.*, 1995, 32, 371. Graphite furnace atomic absorption spectrometry ("GF-AAS") also has the capability for detecting chromium in water to sub-ppb levels. See, R. E. Clement and P. W. Yang, *Anal. Chem.*, 1999, 71, 257R. However, both the ICP-AES and GF-AAS methods can only give information about total chromium concentration in water. A separation procedure, such as solvent extraction, ion chromatography ("IC") or high-pressure liquid chromatography ("HPLC"), must be employed in order to separate Cr(VI) from Cr(III) before detection by ICP-AES or GF-AAS. In addition, the instruments used for these analytical methods are expensive, large and susceptible to environmental noise. It is very difficult to deploy these instruments in field applications.

Ultraviolet visible light absorption spectrometry ("UV/VIS") is a mature technique in analytical chemistry. In photometry and spectrometry, the composition and concentration of dissolved substances are determined by measuring the absorption of light in a liquid that includes such substances. These optical analysis techniques are based on the fact that different substances will absorb light at different wavelengths. See Z. Marczenko, ed., *SpectropHotometric Determination of Elements*, John Willey & Sons Inc., New York, 1976. There are two known UV/VIS methods for chromium detection. The first method is based on the reaction of chromate ions with diphenylcarbazide. The reaction produces a complex which absorbs light with peak absorption at 546 nm. The second method is based on the light absorbing property of the chromate ion itself. Chromate ions in aqueous solution can absorb light with a peak absorption at 373 nm.

Both of the known UV/VIS methods can selectively detect Cr(VI) compounds without interference from Cr(III) compounds. The problem with these methods for monitoring Cr(VI) water contamination is that their sensitivity is too low. The detection limit of the UV/VIS method with diphenylcarbazide as a reagent has been reported to be 20 ppb. The sensitivity of the UVVIS method based on light absorption by chromate ions is 40 times lower than that of diphenylcarbazide method. With present strict drinking water regulations requiring a maximum of 1 ppb Cr(VI) in drinking water, the application of these known methods is limited.

The sensitivity of an optical absorption spectrometric method depends on both the intrinsic property of the light absorber and the path length of the sample cell. According to the Beer-Lambert law, for an absorber in a specific solution, the sensitivity of the optical absorption method has a linear relationship with the path-length of the sample cell. See, D. A. Skoog, D. M. West and F. J. Holler, ed., "Fundamentals of Analytical Chemistry", $7^{th}$ edn., Saunders College Publishing, Fort Worth, 1996, pp. 506–519. The length of the sample cell in conventional UV/VIS absorption spectrometry is normally 1 cm. Sample cells of longer path length are possible, but a 10 cm path length is the limit in normal instruments. Several factors restrict the adoption of a longer path length sample cell in conventional UV/VIS spectrometry. These include the diffusion of the light beam in a long path length sample cell, the availability of intense light from a light source, the limit of the physical size of an instrument, the stray light noise, volume of sample required, etc.

Further, conventional UV/VIS instruments typically use a broadband light source with an optical dispersing element, such as a tungsten lamp coupled to a prism. While being suitable for an analytical laboratory, this type of instrument is unsuitable for field application as it is highly susceptible to damage in field operations.

While not limited thereto in its utility, the present invention has applicability to the field of fiber optics. Liquid core fiber-optic wave guides, i.e., light guide fibers in the form of a capillary filed with a liquid which functions as the light transmitting core, have previously been proposed. Consistent with the teachings of U.S. Pat. No. 3,894,788, the low index of refraction of water and other aqueous liquids rendered it impossible to employ such liquids as the light conducting core medium of a liquid-core, fiber-optic wave guide or the like. However, developments in material science has made long path length UV/VIS possible. Materials having a refractive index of less than water have been developed. For example, a special amorphous fluoropolymer, Teflon AF, developed and marketed by DuPont Fluoroproducts, has a refractive index from 1.29 (Teflon AF 2400) to 1.31 (Teflon AF 1600), which is smaller than that of water.

If a tube made from a material that has a refractive index of less than water is filled with water, the tube will behave as an optical fiber with water as the fiber core. See, R. Altkorn, I. Koev, R. P. Van Duyne and M. Litorja, *Appl. Opt.*, 1997, 36, 8992. Light can be guided into such a water core fiber over a long distance with almost no diffusion loss and can be used as a sample cell in optical spectrometry. As will be appreciated, the interaction with light (absorption, fluorescence, scattering) of any species in the water that fills the tube can be detected.

For examples of such prior liquid core fiber-optic wave guides, reference may be made to U.S. Pat. No. 5,416,879 and U.S. Pat. No. 3,894,788. Further, U.S. Pat. No. 5,570,447 discloses the concept of a liquid core fiber optic waveguide cell for optical spectrometry. The liquid core optical fiber is an amorphous fluoropolymer coated tube filled with water. In U.S. Pat. No. 6,188,813B1, a long path length flow cell, which is an amorphous fluoropolymer tube filled with water, acts as an optical absorption detector for flow injection analysis. U.S. Pat. Nos. 6,011,882 and 6,016,372 disclose amorphous fluoropolymer tubes as sample cells for detecting an optical absorption, fluorescence, and chemiluminescence signal emitted from species diffused into the tube from its surrounding environment. Additionally, U.S. Pat. No. 6,332,049 B1 discloses an amorphous fluoropolymer tube as a sample cell for luminescence detection.

SUMMARY

The present invention overcomes the prior art limitations by providing a hexavalent chromium monitor that is very sensitive, highly reliable, is economical to manufacture and operate, is portable, and allows for accurate field testing of liquids such as water.

In one exemplary embodiment, the hexavalent chromium monitor includes a liquid source containing a liquid, such as water, to be analyzed, a long-path sample cell in the form of a liquid-core waveguide, a light source in communication with the first end of the sample cell for emitting radiation having a wavelength of about and between 350 to 390 nm, a means for monitoring an absorption spectrum of the liquid in the sample cell, and a means for determining the concentration of hexavalent chromium in the liquid.

The sample cell has a first end, an opposed second end, and an interior surface extending therebetween having a refractive index of less than 1.33. The first end of the sample cell is in fluid communication with the liquid source. The sample cell defines an interior core and acts as a receiver for the liquid to be analyzed. In one example, the sample cell is made from Teflon AF and has a minimum length between the first and second ends of 12 cm.

The light source is in communication with the first end of the sample cell for emitting radiation having a wavelength of about and between 350 to 390 nm into the interior core of the waveguide. In one example, the light source may have a bandwidth of about and between 5 to 25 nm.

In one example, the monitoring means of the monitor includes a conventional photodetector in communication with the second end of the sample cell for measuring the absorption of the radiation emitted by the light source by the water in the sample cell. The determining means includes a conventional processor electronically coupled to the photodetector that receives an absorption signal generated by the photodetector and determines a current concentration value of hexavalent chromium in the water.

In an alternative example, the monitor may also include a pH sensor disposed in a flow path of the liquid that generates a pH signal representative of the pH level of the fluid. In this example, the processor is electronically coupled to the pH sensor and the photodetector and the processor determines a current concentration value of hexavalent chromium in the liquid from the received pH and absorption signals.

The hexavalent chromium monitor may also include a first conduit in fluid communication with the liquid source and the first end of the sample cell. A filter element may be disposed in a flow path of the liquid within the first conduit. In one example, the filter is positioned intermediate the liquid source and the first end of the sample cell. The monitor may also include a pump is fluid communication with the liquid source and the first conduit so that, in use, the liquid flows from the liquid source to and through the sample cell.

BRIEF DESCRIPTION OF THE DRAWINGS

The accompanying drawings, which are incorporated in and constitute a part of the specification, illustrate several embodiments of the invention and together with the description, serve to explain the principals of the invention.

DETAILED DESCRIPTION OF THE INVENTION

Figure 1:
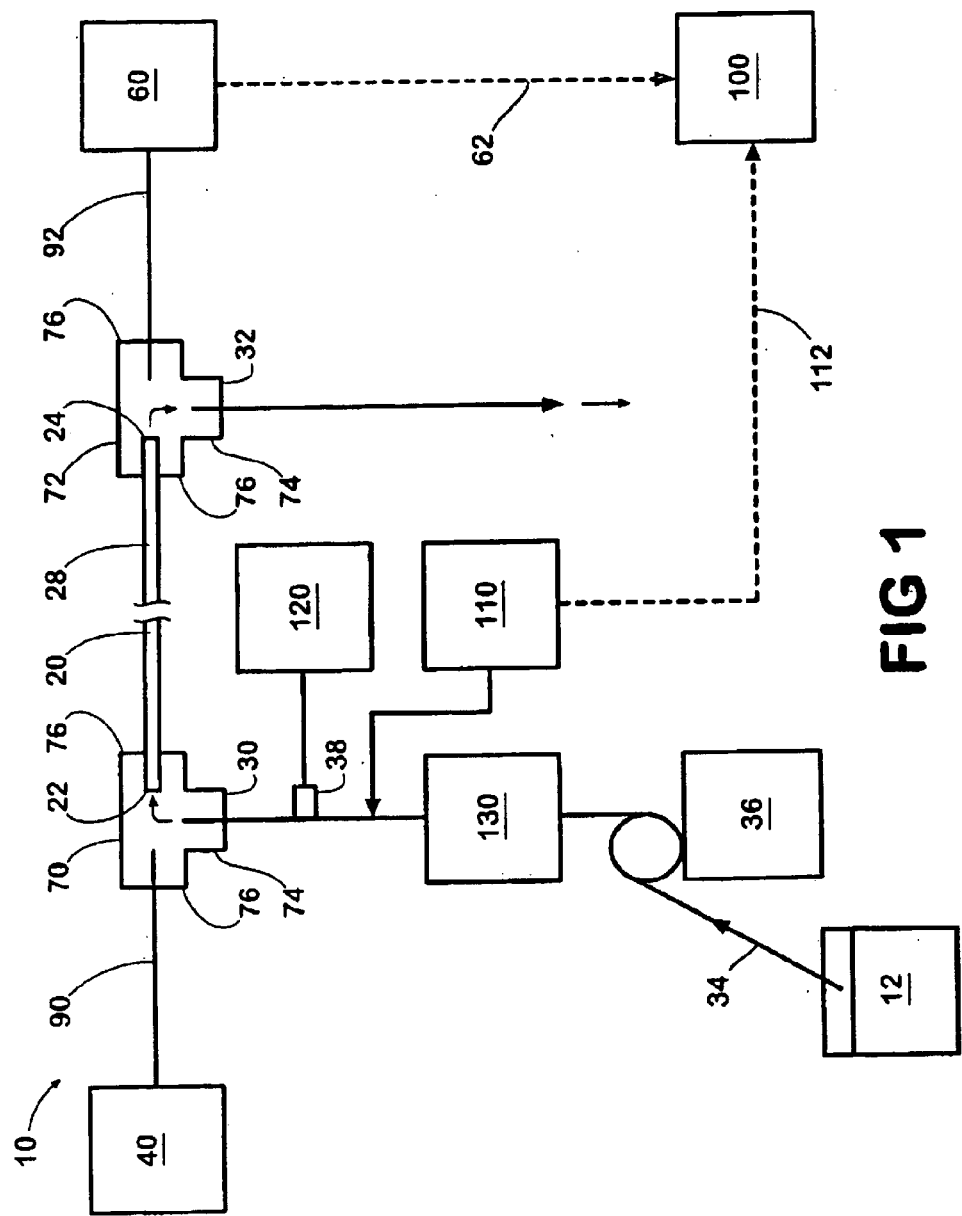
FIG. 1 is a schematic diagram of one embodiment of a Cr(VI) detector of the present invention.
Figure 3:
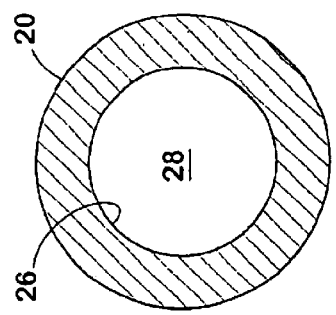
FIG. 3 is a cross-sectional view of an exemplary long-path sample cell.

The present invention is more particularly described in the following examples that are intended to be illustrative only since numerous modifications and variations therein will be apparent to those skilled in the art. As used in the specification and in the claims, the singular form "a," "an" and "the" include plural referents unless the context clearly dictates otherwise.

Referring to the figures, the hexavalent chromium monitor 10 of the present invention may include a long-path sample cell 20, a light source 40, and a photodetector 60. The sample cell is in a form of a liquid-core waveguide and has a first end 22, an opposed second end 24, and an interior surface 26 extending therebetween having a refractive index of less than 1.33. The sample cell defines an interior core 28 and acts as a receiver for a liquid to be analyzed. In one example, the sample cell may be of tubular construction. Further, the sample cell may be made of or coated with a fluoroplymer which is a copolymer of tetrafluoroethylene and perflluoro-2,2-dimethly-1,3-dioxole. An example of a suitable material is manufactured by DuPont Fluoroproducts and is marketed under the tradename Teflon AF. The material that the sample cell 20 is formed from may also be impermeable to liquids, gas, and/or vapor.

The sample cell 20 has a minimum length between the first and second ends of 12 cm. The sample cell can have a length in excess of 200 meters. Preferably, the sample cell has a length between 15 cm and 100 m, which allows for a sensitivity of between about 1.3–0.002 ppb. More preferably, the sample cell has a length between 0.5 m and 50 m, which allows for a sensitivity of between about 0.4–0.0004 ppb. Still more preferably, the sample cell has a length between 1 m and 25 m, which allows for a sensitivity of between about 0.2–0.008 ppb.

Since the length of the sample cell 20 can be meters or even hundreds of meters, the sensitivity of optical spectrometry using the exemplified sample cell can be thousands of times higher than that of conventional optical spectrometry. See, R: Altkom, I. Koev, R. P. Van Duyne and M. Litorja, *Appl. Opt.*, 1997, 36, 8992; P. K. Dasgupta, G. Zhang, S. K. Poruthoor, S. Caldwell and D. Shen, *Anal. Chem.*, 1998, 70, 4661; R. Altkom, I. Koev and M. J. Pelletier, *Appl. Spectrosc.*, 1999, 53, 1169; B. J. Marquardt, P. G. Vahey, R. E. Synovec and L. W. Burgess, *Anal. Chem.*, 1999, 71, 4808; and J. Li and P. K. Dasgupta, *Anal. Chem.*, 2000, 72, 5338. In addition, stray light noise from the surrounding environment is avoided because the efficiency of coupling stray light into the sample cell is very low. Moreover, the sample cell 20 can be bent with very limited loss of light guided in the fiber. It is preferred, therefore, that the sample cell be flexible so that it can be arranged or disposed, such as in a coil, in a limited space so that the monitor can be made compact.

The light source 40 is in communication with the first end 22 of the sample cell and emits radiation into the interior core 28 of the waveguide. Preferably, the light source has a wavelength of about and between 340 to 400 nm; 350 to 390 nm; 360 to 380 nm; 370 to 380 nm; and 370 to 375 nm. Further, the light source has a bandwidth of about and between 3 to 30 nm and, more preferably, of about and between 5 to 25 nm. In one example, the light source 40 may be a UV LED. Such an exemplary light source is the NSHU590 UV LED manufactured by the Nichia Corp. This exemplary light source is a GaN based LED that has a peak emission at 375 nm and a bandwidth of about 15 nm. The light source 40 is powered by a conventional source of energy such as, for example, a battery.

Figure 4:
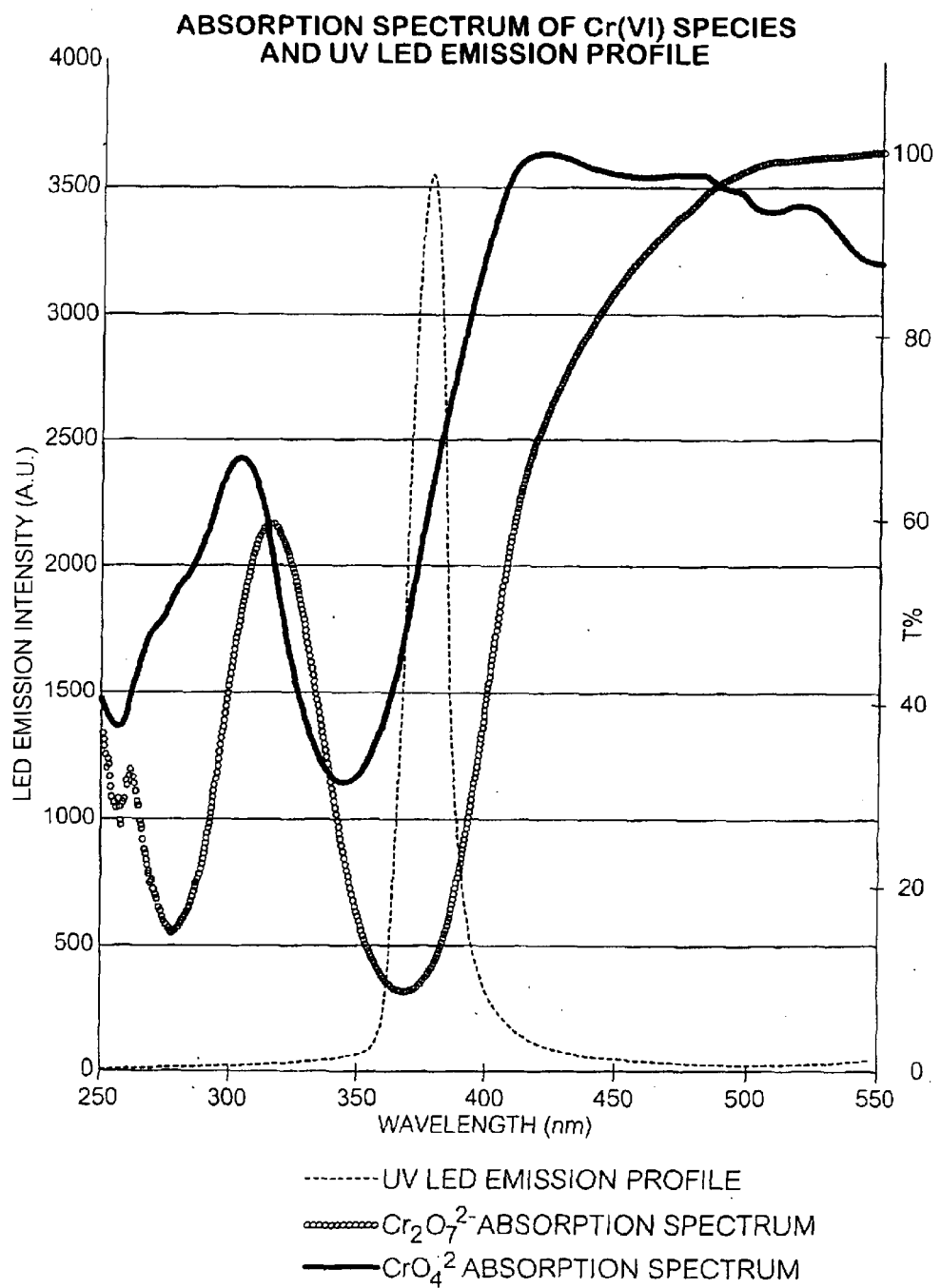
FIG. 4 is a graph showing the UV LED emission profile of one example of the light source of the present invention and the optical absorption spectrum of Cr(VI) species in water.

Referring to FIG. 4, chromate ions in a basic aqueous solution have two absorption bands. One absorption band is peaked at about 280 nm and has a lower sensitivity. The second, higher sensitivity, absorption band is peaked at around 373 nm and is the absorption band of interest in the present invention. Since the bandwidth of the light source is relatively narrow and the absorption spectrum caused by chromate ions is in a band, a dispersing element, such as a prism, grating, and the like, which is normally used in a UV/VIS spectrometer, is not necessary in the monitor of this invention. This allows the monitor 10 to be assembled at lower cost and to be more robust.

A photodetector 60 is in communication with the second end 24 of the sample cell for measuring the absorption of the radiation emitted by the light source 40 by the liquid in the sample cell. The photodetector generates an absorption signal 62 indicative of an uncalibrated concentration of Cr(VI) in the liquid. The photodetector may generate the absorption signal continuously, at discrete or random time intervals, or when directed by the operator. The photodetector 60 is conventional and is exemplified by the PDA55 photodiode, manufactured by ThorLabs, Inc.

Figure 2:
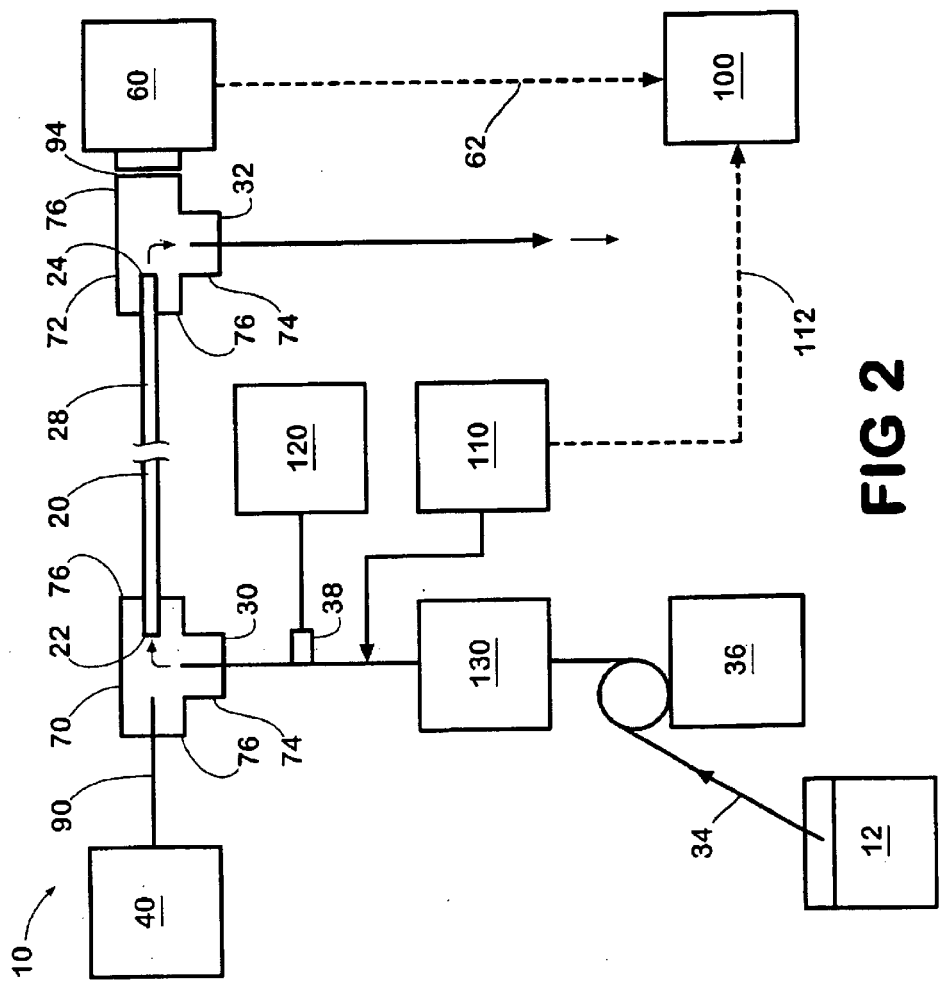
FIG. 2 is a schematic diagram of an alternative embodiment of a Cr(VI) detector of the present invention.

Referring to FIG. 1, in one embodiment of the invention the first end 22 of the sample cell 20 is optically connected to the light source by a first optical fiber 90. Similarly, a second optical fiber 92 can optically connect the second end 24 of the sample cell to the photodetector. Any conventional optical fiber may be utilized such as, for example, a silica optical fiber as exemplified by the FT 1.0 UMT optical fiber manufactured by ThorLabs, Inc. In a second embodiment of the invention shown in FIG. 2, a transparent optical window 94 is disposed proximate the second end 24 of the sample cell intermediate the second end of the sample cell and the photodetector. In this embodiment, the second optical fiber is not required. As one skilled in the art will appreciate, a transparent optical window 94 may also be disposed proximate the first end of the sample cell 20 intermediate the first end of the sample cell and the light source so that the first optical fiber is not required.

The monitor 10 also includes an inlet 30 for admitting the liquid to be analyzed into communication with the first end 22 and interior core 28 of the sample cell. Also, to facilitate movement of the liquid through the sample cell, the monitor 10 may also include an outlet 32 for discharging the liquid. The outlet is in communication with the second end 24 and interior core 28 of the sample cell. Liquid may be directly injected into the sample cell 20 through the inlet 30 for analysis, however it is preferred that a liquid source 12 containing the liquid to be analyzed be provided. The liquid source is in fluid communication with the inlet 30 so that, in use, the liquid flows from the liquid source 12 to the inlet 30, through the interior core 28 of the sample cell, and to the outlet 32 to be discharged.

A first conduit 34 may be provided to place the liquid source into fluid communication with the first end 22 of the sample cell. Preferably the first conduit 34 is coupled to the inlet 30 of the monitor 10. A pump 36, such as for example, an electric pump, may be provided to help move the liquid from the liquid source 12 to and through the sample cell. Such a pump also allows for continuous monitoring of the concentration of Cr(VI) as the liquid flows through the sample cell 20. In one embodiment, the pump 36 may be coupled to the first conduit in a conventional manner such that the pump is in fluid communication with the liquid source and the first conduit. Alternatively, the pump 36 may be placed into fluid communication with the outlet 32 of the monitor 10 so that fluid may be drawn through the sample cell. As one will appreciate, if the liquid source 12 is already pressurized, there is no requirement for a pump.

As shown in FIG. 1, a first hollow member 70 and a second hollow member 72 may be provided. In one embodiment, each respective hollow member has a "T" shape having first and second arms that are perpendicular to each other. The first arm 74 of each respective first and second hollow members 70, 72 defines the respective inlet and outlet of the monitor. Such hollow members are exemplified by the T-shaped connectors manufactured by Ark-Plas Products, Inc. In one embodiment, one of the second arms 76 of the first hollow member is connected to the first end of the sample cell and the other second arm of the first hollow member is coupled to the light source so that radiation is communicated from the light source to the first end of the sample cell. The first optical fiber 90 is connected to the second arm of the first hollow member 70 and the light source 40 so that the light source is optically coupled to the first end 22 of the sample cell.

Similarly, one of the second arms of the second hollow member is connected to the second end of the sample cell and the other second arm of the second hollow member is coupled to the photodetector 60 so that radiation is communicated from the second end of the sample cell to the photodetector. In the embodiment shown in FIG. 1, the second optical fiber 92 is connected to the second arm 76 of the second hollow member 72 and photodetector 60 so that the photodetector is optically coupled to the second end 24 of the sample cell. In the embodiment shown in FIG. 2, the transparent optical window 94 is disposed in the second arm 76 of the second hollow member 72 intermediate the second end 24 of the sample cell and the photodetector so that the photodetector is optically coupled to the second end of the sample cell.

Hexavalent chromium is known to exist as chromate ions in a basic solution but as dichromate ions in an acidic solution. The absorption spectrum of dichromate ions in water is different from that of chromate ions. FIG. 4 shows the absorption spectrum of dichromate ions. The absorption peak of dichromate ions is around 350 nm. This is a broadband absorption. At the wavelength range of the light source emission profile these ions still have absorption, although less sensitive.

In an aqueous solution, Cr(VI) can exist either as chromate ions or as dichromate ions. These two species are in an equilibrium state in a solution. However, the distribution of Cr(VI) in these two species is pH dependent. When the monitor detects the concentration of Cr(VI) in a water sample, both of the species contribute to the obtained absorption signal. Therefore, a pH dependence factor is required to correct the pH dependence of the calibration curve.

Figure 5:
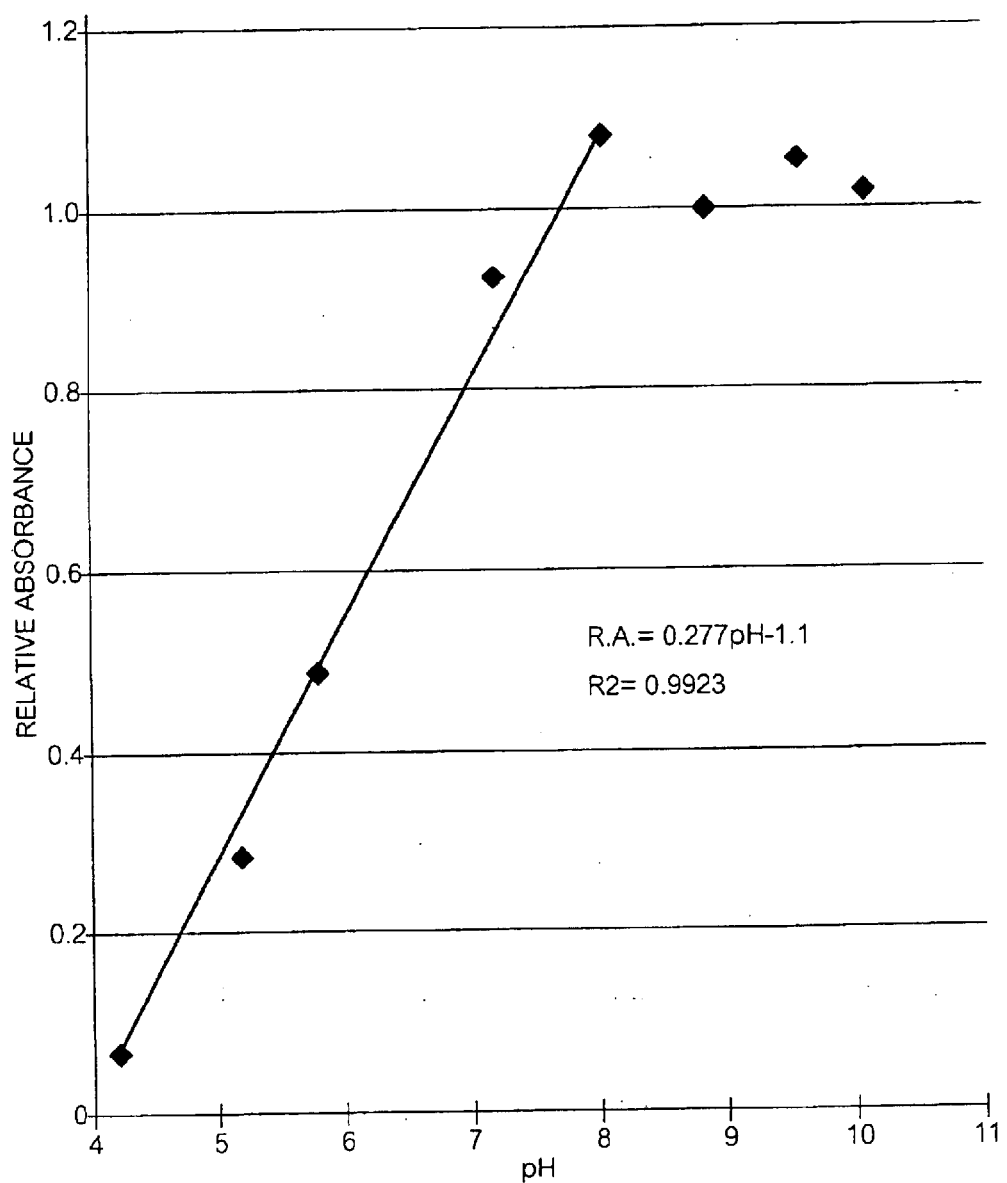
FIG. 5 is a graph showing the pH dependence of a Cr(VI) absorption signal generated by the photodetector.

The pH dependence factor can be obtained by measuring the absorption signal of solutions having the same Cr(VI) concentration but different pH value. As an example, the absorption signal of solutions containing 16 ppb Cr(VI) with different pH is measured with a Cr(VI) monitor of the present invention. The test results are shown in FIG. 5. The absorption signal is independent of the pH value of the solution if the pH of the solution is higher than 8. In the pH range from 4 to 8 the absorption signal can be expressed as:

$$A = A_{(pH=8)} \times (0.277 pH - 1.12)$$

Figure 6:
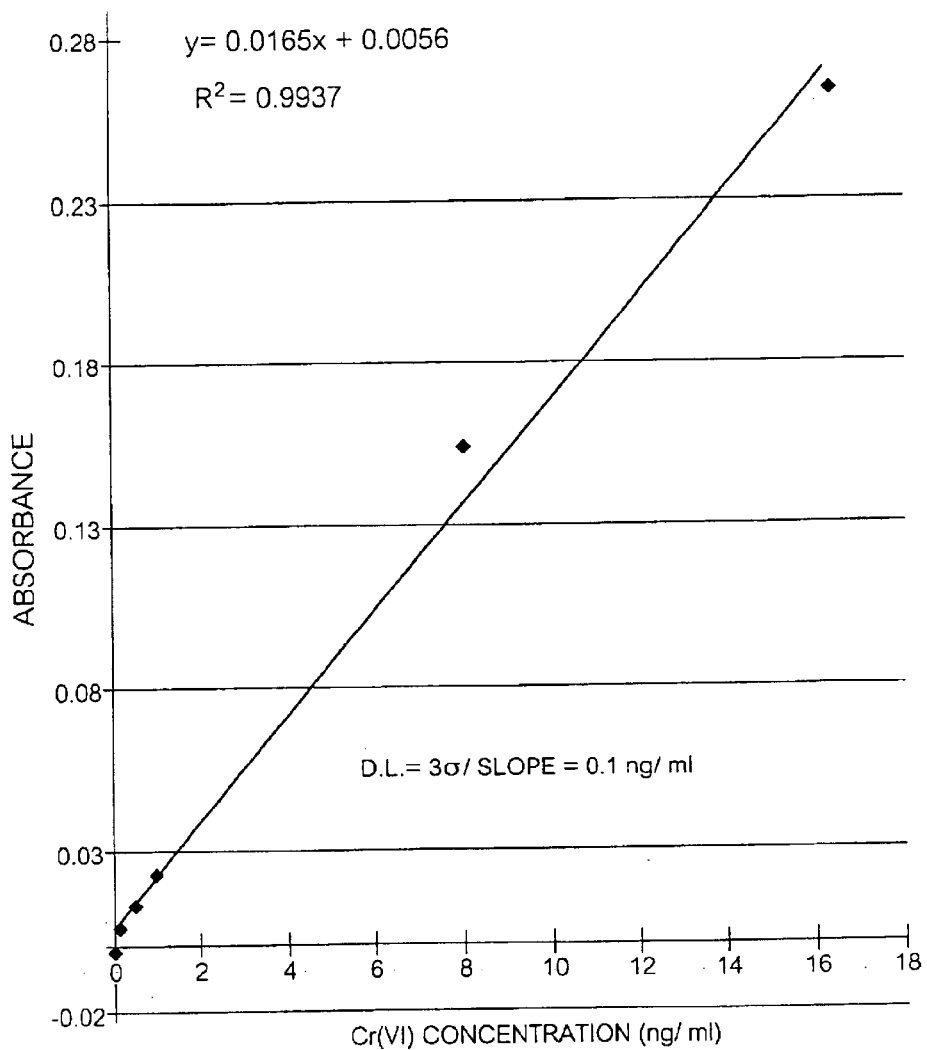
FIG. 6 is a graph showing an exemplary calibration curve of the monitor of the present invention for detecting the concentration of Cr(VI) in water.

An exemplary calibration curve for detecting the concentration of Cr(VI) in a water sample using the Cr(VI) monitor 10 was established by injecting a Cr(VI) containing water sample into the long path length sample cell and recording the absorption signal. As shown in FIG. 6, the relationship between the absorption signal and the concentration of Cr(VI) in the water sample can be expressed as follows when the pH value of the water is higher than 8.

$$Abs. = 0.0165 C_{Cr(VI)} + 0.0056$$

The unit for $C_{Cr(VI)}$ in this equation is ng Cr(VI)/ml. For a water sample with pH in the range from 4 to 8 the absorption signal can be expressed as:

$$Abs. = (0.0165 C_{Cr(VI)} + 0.0056) \times (0.277 pH - 1.12)$$

The detection limit of the monitor 10 for Cr(VI) in a water sample depends on the pH of the water sample. The lowest detection limit is obtained when the pH of the sample is higher than 8. In one example, using an exemplary 2 meter long sample cell and using ground water and drinking water, for which the pH value is normally around 6, the detection limit was about 0.2 ppb.

It must be emphasized that the above equations are merely exemplary and represent the best correlations/predications obtained by statistical analysis on a limited set of measurements. The measurements were not made under optimal research conditions and no attempt was made to select the best data or to determine the reason for readings that departed significantly from the average value. In addition to obtaining larger and more carefully controlled data samples, it is probable that the predictive equations could be further improved by using more sophisticated analysis, such as multiple or geometric regression instead of linear regression.

The determining means of the monitor may include a processor 100 that is electronically coupled to the photodetector 60. The processor receives at least the absorption signal 62 generated by the photodetector and may determine a current concentration value of Cr(VI) in the liquid in the sample cell from at least the absorption signal. For example, in a water sample, if the pH is greater than 8, only the absorption signal 62 generated by the photodetector would be necessary to derive the current concentration value of Cr(VI).

The monitor 10 may also include a pH sensor 110 in fluid communication with the liquid. The pH sensor 110 is conventional and generates a pH signal 112 representative of the pH level of the fluid. As one will appreciate, the pH sensor may be positioned in a flow path of the fluid such as for example, proximate the inlet 30 or outlet 32 of the monitor. The pH sensor 110 may generate the pH signal 112 continuously, at discrete or random time intervals, or when directed by the operator. In one example, the processor 100 is electronically coupled to the pH sensor 110 and the photodetector 60 and receives both the pH and absorption signals. From the received signals, the processor 100 can determine a current concentration value of hexavalent chromium in the liquid.

The processor 100 may be any device for processing the absorption signal 62 and, if required, the pH signal 112 to determine the current value of the concentration of Cr(VI) in the liquid. The processor may be analog or digital and should contain circuits to be programmed for performing mathematical functions such as waveform averaging, amplification, linearization, signal rejection, differentiation, intergration, addition, subtraction, multiplication, and division, where required. Circuits or programs for performing these functions are conventional and well known, and they form no part of the present invention.

In many cases, the preferred processor 100 may be a microcomputer programmed to accomplish the necessary signal processing functions and to deliver the determined concentration of Cr(VI) via line to a display and/or via line to a permanent recording device, such as a printer and/or plotter. A microcomputer has the advantage over dedicated analog or digital processors in that it has the flexibility to be programmed to store and analyze data and to provide hard copy in many different forms.

It is well known that only a very limited number of metal ions such as ferric ions ("$Fe^{3+}$") and uranyl ions ("$UO_2^{2+}$") can absorb light at wavelength around 375 nm. Uranyl ions do not exist in normal ground water or surface water and ferric ions are usually reduced to ferrous ions by the bacteria in ground water. Therefore, the monitor 10 can be used to directly detect the concentration of Cr(VI) in ground water. However, for surface water, such as river or tap water, a chemical reagent such as, for example, hydroxylamine hydrochloride or sodium fluoride, can be added to the liquid prior to the inlet 30 of the monitor 10 to eliminate possible interference from ferric ions. The reagent may be directly injected into the first conduit 34 or reagent from a reagent source 120 may be in selective fluid communication with an inlet port 38 of the first conduit.

The effect of metal ions most commonly existing in ground water and surface water, such as, for example, $Na^+$, $Mg^{2+}$, $Ca^{2+}$, $Cu^{2+}$, $Zn^{2+}$, $Co^{2+}$, $Ni^{2+}$, $Fe^{2+}$, on Cr(VI) detection by the monitor 10 was tested. None of these ions was found to interfere with the detection in the tested concentration range up to 2 ppm. The $Fe^{2+}$ solution used in the interference test was obtained by adding hydroxylamine hydrochloride to $Fe^{3+}$ standard solution. $Cr^{3+}$ ions in water were found to cause an absorption signal, but the sensitivity is 400 times lower than that of chromate ions.

Some organic compounds, such as humic acid in ground water might also absorb the radiation from the light source and cause interference. Such interference from organic species may be eliminated by providing a filter element 130, such as, for example, an active carbon filed column, that is disposed in a flow path of the liquid within the first conduit 34. By positioning the filter element 130 intermediate the liquid source 12 and the inlet 30 of the monitor 10, organic compounds may be absorbed by the filter element prior to the liquid entering the interior core 28 of the sample cell.

EXAMPLE

Detecting Cr(VI) in Waste Water Samples from a Power Plant

The monitor 10 was used to detect Cr(VI) in waste-water samples from a coal fired power plant. The samples were diluted directly with de-ionized water before being injected into the sample cell 20 for optical absorption measurement. The samples were also analyzed using conventional ICP-AES and IC with UV/VIS methods. The analytical result for these samples is listed below. The concentration of Cr(VI) in the samples determined by using the monitor 10 agrees well with the concentration of chromium obtained from ICP-AES. Due to the lack of sensitivity, IC with UV/VIS detection was only able to give a precise result for one sample.

| | Cr(VI) concentration in ppm | | | | | |
|---|---|---|---|---|---|---|
| Sample | Test 1 | Test 2 | Test 3 | Average | ICP Result | IC Result |
| #13 | 36.19 | 38.1 | 36.6 | 37.0 | 36.0 | |
| #14 | 24.1 | 26.3 | 25.3 | 25.2 | 24.1 | |
| #16 | 16.3 | 14.7 | 13.7 | 14.9 | 16.1 | |
| Tower 003 | 37.7 | 41.8 | 40.7 | 40.0 | 45.1 | 35.3 |

The invention has been described herein in detail, in order to comply with the Patent Statutes and to provide those skilled in the art with information needed to apply the novel principles, and to construct and use such specialized components as are required. However, it is to be understood, by those skilled in the art, that the invention can be carried out by specifically different equipment and devices, and that various modifications, both as to equipment details and operating procedures can be affected without departing from the scope of the invention itself. Further, it should be understood that, although the present invention has been described with reference to specific details of certain embodiments thereof, it is not intended that such details should be regarded as limitations upon the scope of the invention except as and to the extent that they are included in the accompanying claims.

We claim:

1. A hexavalent chromium monitor, comprising:
    a) a sample cell in the form of a liquid-core waveguide, the sample cell being of tubular construction and having a first end, an opposed second end, and an interior surface extending therebetween, the sample cell defining an interior core and acting as a receiver for a liquid to be analyzed, the interior surface of the sample cell having a refractive index of less than 1.33;
    b) a light source in communication with the first end of the sample cell for emitting radiation having a wavelength of about and between 350 to 390 nm into the interior core of the waveguide;
    c) a photodetector in communication with the second end of the waveguide for measuring the absorption of the radiation emitted by the light source by the liquid in the sample cell, wherein the photodetector generates an absorption signal;
    d) a processor electronically coupled to the photodetector, wherein the processor receives the absorption signal and determines a current concentration value of hexavalent chromium in the liquid from the absorption signal; and
    e) a pH sensor in fluid communication with the liquid, the pH sensor generating a pH signal representative of the pH level of the fluid.

2. The hexavalent chromium monitor of claim 1, wherein the light source has a bandwidth of about and between 5 to 25 nm.

3. The hexavalent chromium monitor of claim 1, wherein the sample cell is made of or coated with a fluoroploymer which is a copolymer of tetrafluoroethylene and perfluoro-2,2-dimethly-1,3-dioxole.

4. The hexavalent chromium monitor of claim 1, wherein the sample cell is impermeable to liquid.

5. The hexavalent chromium monitor of claim 1, wherein the sample cell is impermeable to gas and vapor.

6. The hexavalent chromium monitor of claim 1, further comprising a first optical fiber, the first optical fiber optically connecting the first end of the sample cell to the light source.

7. The hexavalent chromium monitor of claim 6, further comprising a second optical fiber, the second optical fiber optically connecting the second end of the sample cell to the photodetector.

8. The hexavalent chromium monitor of claim 6, further comprising a transparent optical window disposed in the second end of the sample cell intermediate the second end of the sample cell and the photodetector.

9. The hexavalent chromium monitor of claim 1, further comprising an inlet for admitting the liquid in communication with the first end of the sample cell.

10. The hexavalent chromium monitor of claim 9, further comprising an outlet for discharging the liquid in communication with the second end of the sample cell.

11. The hexavalent chromium monitor of claim 9, further comprising a liquid source of the liquid to be analyzed, the liquid source in communication with the inlet so that, in use, the liquid flows from the inlet through the sample cell to the outlet.

12. The hexavalent chromium monitor of claim 1, wherein the sample cell has a length greater than about 15 cm.

13. The hexavalent chromium monitor of claim 1, wherein the sample cell is formed into a coil.

14. The hexavalent chromium monitor of claim 1, wherein the processor is electronically coupled to the pH sensor and the photodetector, wherein the processor receives the pH signal and the absorption signal and determines a current concentration value of hexavalent chromium in the liquid from the pH signal and the absorption signal.

15. The hexavalent chromium monitor of claim 1, wherein the pH sensor senses the pH of the liquid continuously.

16. The hexavalent chromium monitor of claim 1, wherein the photodetector generates the absorption signal continuously.

17. The hexavalent chromium monitor of claim 1, wherein the pH sensor is disposed in a flow path of the liquid.

18. A hexavalent chromium monitor, comprising:
    a) a liquid source containing a liquid to be analyzed;
    b) a sample cell in the form of a liquid-core waveguide, the sample cell being of tubular construction and having a first end, an opposed second end, and an interior surface extending therebetween, the first end of the sample cell in fluid communication with the liquid source, the sample cell defining an interior core and acting as a receiver for the liquid to be analyzed, the interior surface of the sample cell having a refractive index of less than 1.33;

c) a light source in communication with the first end of the sample cell for emitting radiation having a wavelength of about and between 350 to 390 nm into the interior core of the waveguide;

d) a photodetector in communication with the second end of the sample cell for measuring the absorption of the radiation emitted by the light source by the liquid in the sample cell, wherein the photodetector generates an absorption signal;

e) a processor electronically coupled to the photodetector, wherein the processor receives the absorption signal and determines a current concentration value of hexavalent chromium in the liquid from the absorption signal; and f) a pH sensor in fluid communication with the liquid, the pH sensor generating a pH signal representative of the pH level of the fluid.

19. The hexavalent chromium monitor of claim 18, wherein the light source has a bandwidth of about and between 5 to 25 nm.

20. The hexavalent chromium monitor of claim 18, wherein the sample cell is made of or coated with a fluoroploymer which is a copolymer of tetrafluoroethylene and perfluoro-2,2-dimethly-1,3-dioxole.

21. The hexavalent chromium monitor of claim 18, wherein the sample cell is made from Teflon AF.

22. The hexavalent chromium monitor of claim 18, wherein the sample cell is impermeable to liquid, gas, and vapor.

23. The hexavalent chromium monitor of claim 18, further comprising a first hollow member connected to the first end of the sample cell and defining an inlet in communication with the interior core of the sample cell.

24. The hexavalent chromium monitor of claim 23, further comprising a first optical fiber coupled to the light source and the first hollow member so that radiation is communicated from the light source to the first end of the sample cell.

25. The hexavalent chromium monitor of claim 24, further comprising a second hollow member connected to the second end of the sample cell and defining an outlet in communication with the interior core of the sample cell.

26. The hexavalent chromium monitor of claim 25, further comprising a second optical fiber coupled to the photodetector and the second hollow member so that radiation is communicated from the second end of the sample cell to the photodetector.

27. The hexavalent chromium monitor of claim 25, wherein each respective first and second hollow members has a T-shape having first and second arms perpendicular to each other, wherein the first arm of each respective first and second hollow members forms the respective inlet and outlet.

28. The hexavalent chromium monitor of claim 27, further comprising a transparent optical window disposed in a second arm of the hollow member intermediate the second end of the sample cell and the photodetector.

29. The hexavalent chromium monitor of claim 23, further comprising a first conduit in fluid communication with the liquid source and coupled to the inlet of the first hollow member.

30. The hexavalent chromium monitor of claim 29, wherein the first conduit has an inlet port, further comprising a reagent source in selective fluid communication with the inlet port.

31. The hexavalent chromium monitor of claim 29, further comprising a filter element disposed in a flow path of the liquid within the first conduit, the filter intermediate the liquid source and the inlet of the first hollow member.

32. The hexavalent chromium monitor of claim 29, further comprising a pump in fluid communication with the liquid source and the first conduit so that, in use, the liquid flows from the liquid source, to the inlet, through the sample cell, and to the outlet.

33. The hexavalent chromium monitor of claim 18, wherein the sample cell has a length greater than 15 cm.

34. The hexavalent chromium monitor of claim 18, wherein the processor is electronically coupled to the pH sensor and the photodetector, wherein the processor receives the pH signal and the absorption signal and determines a current concentration value of hexavalent chromium in the liquid from the pH signal and the absorption signal.

35. The hexavalent chromium monitor of claim 18, wherein the pH sensor senses the pH of the liquid continuously.

36. The hexavalent chromium monitor of claim 18, wherein the photodetector generates the absorption signal continuously.

37. The hexavalent chromium monitor of claim 18, wherein the pH sensor is disposed in a flow path of the liquid.

38. A hexavalent chromium monitor, comprising:

a) a liquid source containing a liquid to be analyzed;

b) a sample cell in the form of a liquid-core waveguide, the sample cell being of tubular construction and having a first end, an opposed second end, and an interior surface extending therebetween, the first end in fluid communication with the liquid source, the sample cell defining an interior core and acting as a receiver for the liquid to be analyzed, the interior surface of the sample cell having a refractive index of less than 1.33;

c) a light source in communication with the first end of the sample cell for emitting radiation having a wavelength of about and between 350 to 390 nm into the interior core of the waveguide;

d) means for monitoring an absorption spectrum of the liquid in the sample cell; and e) means for determining the concentration of hexavalent chromium in the liquid;

wherein the determining means comprises a processor and a pH sensor, the processor being electronically coupled to the monitoring means, wherein the processor determines a current value of hexavalent chromium in the liquid based on output received from the monitoring means, wherein the pH sensor is disposed in a flow path of the liquid, the pH sensor in communication with the liquid and generation a pH signal representative of the pH level of the fluid.

39. The hexavalent chromium monitor of claim 30, wherein the monitoring means comprises a photodetector in communication with the second end of the waveguide for measuring the absorption of the radiation emitted by the light source by the liquid in the sample cell; wherein the photodetector generates an absorption signal.

40. The hexavalent chromium monitor of claim 38, wherein the sample cell is made of or coated with a fluoroploymer which is a copolymer of tetrafluoroethylene and perfluoro-2,2-dimethly-1,3-dioxole.

41. The hexavalent chromium monitor of claim 38, wherein the sample cell is made from Teflon AF.

42. The hexavalent chromium monitor of claim 38, wherein the sample cell has a length greater than 15 cm.

43. The hexavalent chromium monitor of claim 38, wherein the light source has a bandwidth of about and between 5 and 25 nm.

44. The hexavalent chromium monitor of claim 38, wherein the sample cell is impermeable to liquid, gas, and vapor.

45. The hexavalent chromium monitor of claim 38, wherein the sample cell is flexible.

46. The hexavalent chromium monitor of claim 39, wherein the determining means comprises a processor electronically coupled to the photodetector, wherein the processor receives the absorption signal and determines a current concentration value of hexavalent chromium in the liquid from the absorption signal.

47. The hexavalent chromium monitor of claim 46, wherein the processor is electronically coupled to the pH sensor and the photodetector, wherein the processor receives the pH signal and the absorption signal and determines a current concentration value of hexavalent chromium in the liquid from the pH signal and the absorption signal.

48. The hexavalent chromium monitor of claim 38, further comprising a first conduit in fluid communication with the liquid source and the first end of the sample cell.

49. The hexavalent chromium monitor of claim 48, wherein the first conduit has an inlet port, further comprising a reagent source in selective fluid communication with the inlet port.

50. The hexavalent chromium monitor of claim 48, further comprising a filter element disposed in a flow path of the liquid within the first conduit, the filter intermediate the liquid source and the first end of the sample cell.

51. The hexavalent chromium monitor of claim 48, further comprising a pump is fluid communication with the liquid source and the first conduit so that, in use, the liquid flows from the liquid source through the sample cell.

52. A hexavalent chromium monitor, comprising:
   a) a sample cell in the form of a liquid-core waveguide, the sample cell being of tubular construction and having a first end, an opposed second end, and an interior surface extending therebetween, the sample cell defining an interior core and acting as a receiver for a liquid to be analyzed, the interior surface of the sample cell having a refractive index of less than 1.33;
   b) a light source in communication with the first end of the sample cell for emitting radiation having a wavelength of about and between 350 to 390 nm into the interior core of the waveguide;
   c) a photodetector in communication with the second end of the waveguide for measuring the absorption of the radiation emitted by the light source by the liquid in the sample cell; and
   d) a pH sensor in fluid communication with the liquid, the pH sensor generating a pH signal representative of the pH level of the fluid.

53. A hexavalent chromium monitor, comprising:
   a) a liquid source containing a liquid to be analyzed;
   b) a sample cell in the form of a liquid-core waveguide, the sample cell being of tubular construction and having a first end, an opposed second end, and an interior surface extending therebetween, the first end of the sample cell in fluid communication with the liquid source, the sample cell defining an interior core and acting as a receiver for the liquid to be analyzed, the interior surface of the sample cell having a refractive index of less than 1.33;
   c) a light source in communication with the first end of the sample cell for emitting radiation having a wavelength of about and between 350 to 390 nm into the interior core of the waveguide;
   d) a photodetector in communication with the second end of the sample cell for measuring the absorption of the radiation emitted by the light source by the liquid in the sample cell; and
   e) a pH sensor in fluid communication with the liquid, the pH sensor generating a pH signal representative of the pH level of the fluid.

54. A hexavalent chromium monitor, comprising:
   a) a liquid source containing a liquid to be analyzed;
   b) a sample cell in the form of a liquid-core waveguide, the sample cell being of tubular construction and having a first end, an opposed second end, and an interior surface extending therebetween, the first end in fluid communication with the liquid source, the sample cell defining an interior core and acting as a receiver for the liquid to be analyzed, the interior surface of the sample cell having a refractive index of less than 1.33;
   c) a light source in communication with the first end of the sample cell for emitting radiation having a wavelength of about and between 350 to 390 nm into the interior core of the waveguide;
   d) means for monitoring an absorption spectrum of the liquid in the sample cell; and
   e) means for determining the concentration of hexavalent chromium in the liquid,
   wherein the determining means comprises a pH sensor disposed in a flow path of the liquid, the pH sensor in communication with the liquid and generating a pH signal representative of the pH level of the fluid.

* * * * *